United States Patent [19]

Silbert et al.

[11] 4,262,137

[45] Apr. 14, 1981

[54] PREPARATION OF ISOPROPENYL ESTERS OF DICARBOXYLIC ACIDS

[75] Inventors: Leonard S. Silbert; Samuel Serota, both of Philadelphia, Pa.

[73] Assignee: The United States of America as represented by the Secretary of Agriculture, Washington, D.C.

[21] Appl. No.: 835,103

[22] Filed: Sep. 21, 1977

[51] Int. Cl.$^3$ .................... C07C 69/767; C07C 69/82; C07C 69/48; C07C 69/50
[52] U.S. Cl. ........................................ 560/95; 560/201
[58] Field of Search ................................. 560/95, 201

[56] References Cited

U.S. PATENT DOCUMENTS

| | | | |
|---|---|---|---|
| 2,411,962 | 12/1946 | Freed | 560/95 |
| 2,466,738 | 4/1949 | Phillips | 560/201 |
| 3,574,717 | 4/1971 | Lloyd | 560/95 |
| 3,941,741 | 3/1976 | De Zuba et al. | 260/37 SB |
| 4,020,123 | 4/1977 | Trapasso | 260/837 R |

FOREIGN PATENT DOCUMENTS

| | | | |
|---|---|---|---|
| 824856 | 12/1959 | United Kingdom | 560/95 |
| 833471 | 4/1960 | United Kingdom | 560/95 |
| 1037897 | 8/1966 | United Kingdom | 560/95 |

OTHER PUBLICATIONS

Rothman et al, J. Org. Chem., 31, 629–630 (1966).

*Primary Examiner*—Howard T. Mars
*Assistant Examiner*—Vera C. Clarke
*Attorney, Agent, or Firm*—M. Howard Silverstein; William E. Scott; David G. McConnell

[57] ABSTRACT

Isopropenyl esters and half isopropenyl ester-half carboxylic acid products are prepared by reacting at a temperature of about 150°–160° C. at maximum pressures of from about 400 to 1000 psi for about 10 to 20 hours in the presence of a suitable catalyst and in N-methyl-2-pyrrolidone, a saturated or unsaturated aliphatic or aromatic dicarboxylic acid with methylacetylene or with a gas containing a mixture of methylacetylene, allene and some inert short chain hydrocarbons.

8 Claims, No Drawings

PREPARATION OF ISOPROPENYL ESTERS OF DICARBOXYLIC ACIDS

BACKGROUND OF THE INVENTION

1. Field of the Invention

This invention relates to the preparation of isopropenyl esters of dicarboxylic acids and more particularly to the synthesis of isopropenyl esters of saturated and unsaturated aliphatic and aromatic dicarboxylic acids and also to the synthesis of the half isopropenyl ester-half carboxylic acid products from the same dicarboxylic acids.

2. Description of the Prior Art

Isopropenyl esters of dicarboxylic acids are not new; they have been prepared previously as described in British patent 1,037,897 and in J. Org. Chem., 31, 629, 1966. However, the processes described by both of these references use toxic and poisonous catalysts such as boron trifluoride and mercury salts.

Compounds such as our half isopropenyl ester-half carboxylic acid compounds have not, to our knowledge, been reported as the major products of a reaction, but only as minor co-products in the preparation of diisopropenyl esters.

SUMMARY OF THE INVENTION

An object of this invention is to provide a method of preparing isopropenyl esters of dicarboxylic acids.

Another object is to provide a method of preparing enol esters of dicarboxylic acids that does not use toxic and poisonous catalysts such as boron trifluoride and mercury salts.

A further object is to provide a method of preparing half isopropenyl ester-half carboxylic acid products from saturated and unsaturated aliphatic and aromatic dicarboxylic acids.

In general, the above objects are accomplished by a process in which a saturated or unsaturated aliphatic dicarboxylic acid having up to 22 carbon atoms or an aromatic dicarboxylic acid is reacted in N-methyl-2-pyrrolidone with methylacetylene or with a gas containing about 64–66 mole percent of approximately a 50—50 mixture of methylacetylene and allene (propadiene) and about 36–34 mole percent of $C_3$ to $C_5$ hydrocarbons (this is known in the art as MAPP gas which is the registered trademark of a fuel introduced by the Dow Chemical Company which, as noted above, basically comprises a mixture of methylacetylene, allene, propane and propylene) in the presence of a suitable catalyst at a temperature of about 150°–160° C. and maximum pressures of about 400 to 1000 psi for about 10 to 20 hours. When the desired produce is a half isopropenyl ester-half carboxylic acid, the catalytic conditions are modified as hereafter described.

DETAILED DESCRIPTION OF THE INVENTION

Saturated or unsaturated aliphatic or aromatic dicarboxylic acids are reacted with methyl acetylene or with a gas such as MAPP gas, the major proportion of which is a mixture of methylacetylene and allene, in the presence of a suitable solvent and a suitable catalyst. Dicarboxylic acids having from 2 to 22 carbon atoms in their structure may be used in the process of this invention.

Azelaic, sebacic, terephthalic and fumaric acids are more preferred for use with this invention.

We unexpectedly found that N-methyl-2-pyrrolidone is the most suitable solvent for the purposes of our invention. When other solvents such as ethyl acetate, dioxane, 1,2-dichloroethane, 1,1,2,2,-tetrachloroethane, methylene chloride, acetone, chloroform, tetrahydrofuran, and ethyl alcohol were used, a polymeric salt formed with the diacid and the catalyst and precipitated out of solution. Although there appeared to be no reason why the same type of precipitate would not form with N-methyl-2-pyrrolidone, when we tried this solvent, we were surprised to find that no precipitate formed and the reaction proceeded as desired.

A variety of transition metal compounds, especially salts, are useful in preparing catalysts for this reaction. The preferred cation components are selected from group II B and VIII of the Periodic Table; the more preferred from these two groups, in descending order of preference, are zinc, mercury, cadmium, and palladium. The preferred anions are inorganic; preferably halides, nitrates and sulfates. However, the reaction may be modified by appropriate catalytic conditions to produce only the half isopropenyl ester-half carboxylic acid. In one modification, the inorganic salt such as zinc chloride is used in solutions in the presence of ammonium chloride and/or ammonium hydroxide. In another modification, the anion component of the catalyst is an organic type exemplified by acetylacetonate, i.e., zinc acetylacetonate or other 1,3-diketones; these also lead to conversion of only one of the two carboxylic acid functionalities in dibasic acids to the isopropenyl ester. Mixtures of these transition metal salts may also be used. In our experimental work with the process of the invention, we have found zinc chloride to be the most preferred catalyst.

Methyl acetylene is the preferred reactant with the dicarboxylic acids. However, MAPP gas is a very suitable substitute and is more economically feasible. The short chain saturated and unsaturated aliphatic hydrocarbons found in some MAPP gases do not interfere with the process of this invention. In using MAPP gas to prepare isopropenyl stearate, it has been observed that when the reaction was run at temperatures higher than about 160° C. the quantities of ester obtained were larger than the stoichiometric amounts that would be expected from the reaction of the methylacetylene present in the gas. This shows that the allene in the MAPP gas was converted to methylacetylene and that allene itself could be used to prepare diisopropenyl esters.

Although a wide variation in temperatures and pressures may be used in our process, we found that conducting the reaction at about 150°–160° C. at about 400 to 1000 psi for from 10 to 20 hours was very suitable.

Our invention is illustrated in further detail in the following examples wherein the reaction products were analyzed by one or more of the following methods: gas-liquid chromatography (GLC), column chromatography, mass spectrometry, infrared analysis (IR), and nuclear magnetic resonance (NMR).

EXAMPLE 1

Preparation of isopropenyl hydrogen sebacate:

A 1-liter pressure vessel equipped with a magnetic stirrer, a thermocouple, a thermocontroller, a methyl acetylene reservoir tank, a pressure burette, a gas line, and a control valve, was flushed free of air with nitrogen and charged with 100 ml (1.04 moles) of N-methyl-2-pyrrolidone; 10.0 gm (0.0038 moles) of zinc acetylacetonate; 25.0 gm. (0.12 moles) sebacic acid; 11.0 gms (0.61 moles) water; 5.0 gm (0.093 moles) ammonium chloride; and 135 ml of MAPP gas (65 mole percent methyl acetylene and allene), and heated to 155° C. at a maximum pressure of 550 psi with stirring for about 14 hours. The reaction vessel was allowed to cool at room temperature and an aliquot removed. The aliquot was shaken with diethyl ether and water and the ether layer dried with magnesium sulphate and evaporated to dryness. An infrared spectrum of the dried product in carbon disulphide solution showed quantitative conversion to isopropenyl hydrogen sebacate. The IR spectrum was identical to that of a pure reference sample.

EXAMPLE 2

Preparation of isopropenyl hydrogen sebacate:

The pressure vessel described in Example 1 was charged as follows: 5.0 gm (0.037 moles) zinc chloride plus 0.50 gm. (0.01 moles) ammonium chloride was dissolved with warming in 10.0 ml (0.074 moles) of ammonium hydroxide, and after cooling to ambient room temperature (about 20°-24° C.), 1.0 ml (0.0074 moles) ammonium hydroxide was added and the mixture was poured into the pressure vessel with 25.0 gm (0.12 moles) of sebacic acid dissolved in 100 ml (1.04 moles) Of N-methyl-2-pyrrolidone. The pressure vessel was sealed, flushed free of air with nitrogen, 135 mls (3.37 moles) of methyl acetylene was added and the vessel heated to 150° C. at a maximum pressure of 515 psi with stirring, for about 14 hours. After work-up as in Example 1, IR analysis showed quantitative conversion to isopropenyl hydrogen sebacate.

EXAMPLE 3

Preparation of diisopropenyl azelate:

The pressure vessel described in Example 1 was charged with 100.0 ml (1.04 moles) of N-methyl-2-pyrrolidone solution containing 25.0 gm. (0.13 moles) azelaic acid, then 5.0 gm (0.037 moles) zinc chloride was added and dissolved by heating and stirring. After cooling to room temperature, sealing and flushing with nitrogen, 140 mls of MAPP gas (65 mole percent methyl acetylene and allene) was added and the charge heated with stirring at 155° C. at a maximum pressure of 430 psi for about 19.5 hours. After work-up as in Example 1, IR showed the product to be essentially pure diisopropenyl azelate with a trace of azelaic acid and azelaic anhydride.

EXAMPLE 4

Preparation of diisopropenyl terephthalate:

The reaction described in Example 3 was repeated using 27.0 gm (0.162 moles) of terephthalic acid instead of azelaic acid. Infrared analysis of an aliquot of the product showed several materials present. Methylation of a representative portion of the product with diazomethane and analysis of the methylated product by GLC showed the product to be predominantly the half-ester with a smaller amount of the diisopropenyl ester. We anticipate that higher yields of diisopropenyl terephthalate can be obtained if the rate of reaction is increased by conducting it at higher temperatures and pressures. Pure diisopropenyl terephthalate was obtained by passing an aliquot of the above mixed reaction products through a short plug of Florisil (a magnesium silicate) and eluting with petroleum ether. The product crystallized in rhombic shaped plates from petroleum ether, m.p. 72°-73.5° C. Carbon and hydrogen analysis: calculated % C 68.29, % H 5.96; found % C 69.05, % H 5.58. Infrared examination of the crystals in carbon disulphide solution shows band maxima at 1737, 1263, 1210, 1110, 1092, 1017, 867, and 720 cm$^{-1}$. NMR analysis in deuterochloroform shows absence of the

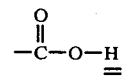

proton signal in the chromatographed, recrystallized sample. The mass spectrum pattern of the unpurified product, m/e 189(100%), 161(50%), 132(10%), is indicative of the diisopropenyl ester. Reactants and products for this example are shown in Table I.

EXAMPLES 5-9

These examples, in which azelaic acid was reacted with MAPP gas were carried out in the same fashion as Examples 1-4. Reactants and products are shown in Table I.

TABLE I

| Ex. | MAPP Gas ml | Dicarboxylic Acid moles | ZnCl$_2$ moles | Molar Ratio Acid to Catalyst | N-methyl-2-pyrrolidone ml | H$_2$O ml | NH$_4$OH ml | NH$_4$Cl gm | Temp/Pressure/Time °C. | psi | Hrs | Dicarboxylic Ester % | ½ Ester ½ Acid % | Unreacted Dicarboxylic Acid % |
|---|---|---|---|---|---|---|---|---|---|---|---|---|---|---|
| 4 | 160 | 0.162 | 0.039 | 4.1 | 100 | 0 | 0 | 0 | 150 | 430 | 20 | 25 | 50 | 25 |
| 5 | 400 | 0.387 | 0.147 | 2.6 | 250 | 0 | 0 | 0 | 150 | 700 | 20 | 94 | 1.5 | 4.5 |
| 6 | 400 | 0.387 | 0.147 | 2.6 | 250 | 10 | 0 | 0 | 150 | 950 | 20 | 78 | 21 | 1 |
| 7 | 400 | 0.387 | 0.147 | 2.6 | 250 | 40 | 0 | 0 | 160 | 970 | 20 | 13 | 46 | 42 |
| 8 | 320 | 0.266 | 0.075 | 3.55 | 200 | 0 | 20 | 1 | 150 | 870 | 20 | 54 | 42 | 4 |
| 9 | 320 | 0.266 | 0.075 | 3.55 | 200 | 0 | 40 | 0 | 160 | 890 | 20 | 21.5 | 72.5 | 6 |

We claim:

1. A process for preparing isopropenyl esters of dicarboxylic acids comprising reacting a dicarboxylic acid selected from the group consisting of saturated and unsaturated aliphatic dicarboxylic acids having up to 22 carbon atoms and aromatic dicarboxylic acids in N-methyl-2-pyrrolidone with a gas selected from the group consisting of methylacetylene and a gas containing about 64 to 66 mole percent of approximately a 50—50 mixture of methylacetylene and allene and about 34 to 36 mole percent of hydrocarbons having carbon chain lengths of from 3 to 5, said reaction being conducted in the presence of a catalyst selected from the group consisting of those transition metal compounds in which the cation component is selected from the group consisting of zinc, mercury, cadmium, and palladium, and the anion component is selected from the group consisting of halides, nitrates, sulfates, and acetylacetonate, and at a temperature of about 150°-160° C. at about 400 to 1000 p.s.i. for about 10 to 20 hours.

2. The process of claim 1 wherein the catalyst is zinc chloride.

3. The process of claim 1 wherein the catalyst is zinc acetylacetonate.

4. The process of claim 1 wherein the catalytic conditions are modified by the addition of an ammonium salt.

5. The process of claim 1 wherein the dicarboxylic acid is sebacic acid.

6. The process of claim 1 wherein the dicarboxylic acid is azelaic acid.

7. The process of claim 1 wherein the dicarboxylic acid is terephthalic acid.

8. The process of claim 1 wherein the dicarboxylic acid is fumaric acid.

* * * * *